United States Patent
Fries

(10) Patent No.: US 6,410,745 B1
(45) Date of Patent: Jun. 25, 2002

(54) PROCESS FOR PREPARING 1-GUANYLPYRAZOLE ACID ADDUCTS

(75) Inventor: Guido Fries, Recklinghausen (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/972,897

(22) Filed: Oct. 10, 2001

(30) Foreign Application Priority Data

Oct. 13, 2000 (DE) .......................... 100 50 900

(51) Int. Cl.[7] .......................... C07D 231/12
(52) U.S. Cl. .................................. 548/375.1
(58) Field of Search ....................... 548/375.1

(56) References Cited

U.S. PATENT DOCUMENTS 5,453,514 A    9/1995   Niigata et al.

FOREIGN PATENT DOCUMENTS

DE    42 37 687 A1    5/1994
WO    WO 97/30972     8/1997

OTHER PUBLICATIONS

Bernatowicz, et al., "1H–Pyrazole–1–carboxamidine Hydrochloride: An Attractive Reagent for Guanylation of Amines and Its Application to Peptide Synthesis", *J. Org. Chem.*, vol. 57, pp. 2497–2502, 1992.

Bernatowicz, et al., "1–H Pyrazole–1–carboxamidine Hydrochloride: An Attractive Reagent for Guanylation of Amines and Its Application to Peptide Synthesis" J. ORG. CHEM., (1992), vol. 57, No. 8, pp. 2497–2502.

Lee et al., "1H–Pyrazole–1–carboxamidines: New Inhibitors of Nitric Oxide Synthase", Bioorganic & Medicinal Chemistry Letters (2000), vol. 10, pp. 2771–2774.

*Primary Examiner*—Robert W. Ramsuer
(74) *Attorney, Agent, or Firm*—Oblon, Spivak, McClelland, Maier & Neustadt, P.C.

(57) ABSTRACT

1-Guanylpyrazole acid adducts of the formula:

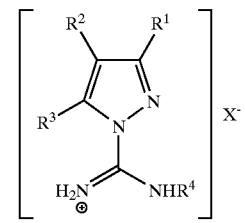

wherein $R^1$, $R^2$ and $R^3$ independently of one another are hydrogen, a branched or straight-chain $C_{1-6}$-alkyl group, a $C_{3-8}$-cycloalkyl group or a $C_{6-12}$-aryl group which is unsubstituted or substituted by 1 to 6 alkyl groups;

$R^4$ is hydrogen or a straight-chain or branched $C_{1-4}$-alkyl group; and

X is Cl or Br, are prepared by a process which comprises: conducting the reaction of pyrazole or a derivative thereof with cyanamide or a derivative thereof and gaseous hydrogen chloride or hydrogen bromide in an aprotic solvent.

12 Claims, No Drawings

PROCESS FOR PREPARING 1-GUANYLPYRAZOLE ACID ADDUCTS

BACKGROUND OF THE INVENTION

1. Field of the Invention

The present invention relates to a process for preparing 1-guanylpyrazole acid adducts of the formula:

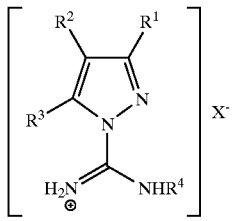

wherein $R^1$, $R^2$ and $R^3$ independently of one another are a hydrogen atom, a branched or straight-chain alkyl group having 1 to 6 carbon atoms, a cycloalkyl group having 3 to 8 carbon atoms or an aryl group having a total of 6 to 12 carbon atoms and being unsubstituted or substituted by 1 to 6 alkyl groups, $R^4$ is a hydrogen atom or a straight-chain or branched alkyl group having 1 to 4 carbon atoms and X is Cl or Br, by reacting pyrazole or its derivatives with cyanamide or its derivatives and gaseous hydrogen chloride or hydrogen bromide in aprotic solvents and work-up by a mechanical separating operation and, if appropriate, thermal aftertreatment.

2. Description of the Background

1-Guanylpyrazole acid adducts of the formula above where X=Cl or Br (1H-pyrazole-1-carboxamidine hydrohalides and their derivatives) can be used as nitrification inhibitors and for the guanylation of amines, for example, for the conversion of ornithine into arginine.

Syntheses of 1H-pyrazole-1-carboxamidine hydrochloride and its derivatives from pyrazole or substituted pyrazole representatives, cyanamide and acids are known as described in the literature. Thus, German patent application DE 42 37 687 A1 discloses a process in which substituted 1H-pyrazoles are reacted with aqueous cyanamide liquor with addition of at least equimolar quantities of an acid. A great disadvantage of this process is the fact that organically polluted wastewater is produced which requires disposal.

J. Org. Chem. 1992, 57, page 2497, describes the preparation of 1H-pyrazole-1-carboxamidine hydrochloride by refluxing pyrazole with cyanamide in a 4 N p-dioxane/HCl solution for two hours. However, because of the fact that explosive peroxides are easily formed, the use of the solvent p-dioxane in the process is a serious disadvantage. A need continues to exist for improvements in the process of producing 1-guanylpyrazole acid adducts which avoid these known disadvantages.

SUMMARY OF THE INVENTION

Accordingly, one object of the present invention to provide a process for preparing 1H-pyrazole-1-carboxamidine hydrochloride or hydrobromide or its derivatives, which is technically simple and does not require the use of a solvent such as p-dioxane or other ether solvents that readily form peroxides and where no aqueous acid is used, so that no waste is produced, which normally requires complicated and costly procedures of disposal.

Briefly, this object and other objects of the present invention as hereinafter will become more readily apparent can be attained by a process for preparing 1-guanylpyrazole acid adducts of the formula

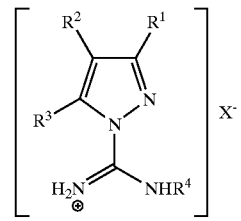

wherein $R^1$, $R^2$ and $R^3$ independently of one another are hydrogen, a branched or straight-chain $C_{1-6}$-alkyl group, a $C_{3-8}$-cycloalkyl group or a $C_{6-12}$-aryl group either unsubstituted or substituted by 1 to 6 alkyl groups, $R^4$ is hydrogen or a straight-chain or branched $C_{1-4}$-alkyl group, such as, for example, a methyl, ethyl, isopropyl or tert-butyl group, and X is Cl or Br, by reacting pyrazole or a derivative thereof with cyanamide or a derivative thereof and gaseous hydrogen chloride or hydrogen bromide in an aprotic solvent.

DETAILED DESCRIPTION OF THE PREFERRED EMBODIMENTS

Applicants have now discovered a method by which 1H-pyrazole-1-carboxamidine hydrochloride or hydrobromide and its derivatives can be produced which does not result in the formation of peroxides and which does not use gaseous hydrogen chloride or hydrogen bromide in the reaction. This objective has been accomplished by reacting pyrazole or a derivative thereof with cyanamide or a derivative thereof in an aprotic solvent.

Work-up of the product of the present reaction is generally conducted by a mechanical separating operation, for example, by filtration, membrane filtration, decanting or centrifugation, and, if appropriate, thermal aftertreatment, for example drying, preferably under reduced pressure.

Thus, the process for preparing 1H-pyrazole-1-carboxamidine hydrochloride or hydrobromide and its derivatives comprises, in particular, the following reaction and process steps:

reaction of pyrazole or a pyrazole derivative with cyanamide or a cyanamide derivative and gaseous hydrogen chloride or hydrogen bromide, mechanical separation of the carboxamidine hydrochloride or hydrobromide formed and if appropriate, thermal treatment of the isolated crude carboxamidine hydrochloride or hydrobromide (in particular to remove adhering residual solvents).

Suitable solvents which are suitable for the process of the invention include aprotic polar solvents. Examples of such suitable solvents are chlorinated hydrocarbons, for example 1,2-dichloroethane, dichloromethane and trichloromethane, sulfoxides, sulfones and sulfolanes; for example ,dimethyl sulfoxide, diisopropyl sulfone, sulfolane, 2-methylsulfolane, 3-methylsulfolane and 2-methyl-4-butylsulfolane; ketones, for example acetone, methyl ethyl ketone, methyl isobutyl ketone or cyclohexanone; ethers, for example, methyl tert-butyl ether, diphenyl ether, diisopropyl ether, anisole and dimethoxyethane, polyethers, for example diethylene glycol dimethyl ether, and also nitriles, for example acetonitrile. Dimethoxyethane is preferred as the solvent.

The temperatures of the reaction ranges from −20° C. to 150° C., preferably from 0° C. to 100° C. and particularly preferably from 60° C. to 90° C. A reaction temperature ranging from about 70° C. to about 85° C. is very particularly preferred.

The reaction is conducted at a pressure ranging from 0.1 bar to 50 bar, preferably from 1 bar to 10 bar. Particularly preferably, the reaction is conducted at a pressure of about 1 bar (atmospheric pressure). The amount of hydrogen chloride or hydrogen bromide gas introduced is adjusted such that the consumption is as quantitative as possible and the waste gas contains as little unreacted hydrogen chloride or hydrogen bromide as possible. Hydrogen chloride is preferred as the acid.

The process can be carried out batchwise or continuously.

In the case of batch-wise operation, the reaction will have ended after from about 15 minutes to 8 hours, preferably from 30 minutes to 4 hours, in particular from 45 minutes to 60 minutes. Thus, surprisingly, it has been found that the use of gaseous hydrogen chloride or hydrogen bromide, in particular hydrogen chloride, which passes through the reaction solution, preferably results in the reaction time described in J. Org. Chem. 1992, 57, page 2497 being halved, thus leading to a considerably increased space/time yield.

Subsequently, the reaction mixture is cooled, the precipitated solid is separated, preferably by using a mechanical separating operation such as normal filtration or membrane filtration or separation by centrifugation or decanting, and is, if appropriate, subjected to thermal aftertreatment, preferably drying, in particular under reduced pressure. Further purification is generally not necessary. However, in particular cases, for example, in the case of particularly high purity requirements, recrystallization or any other suitable purification operation known per se may also be conducted.

Having now generally described this invention, a further understanding can be obtained by reference to certain specific Examples which are provided herein for purposes of illustration only and are not intended to be limiting unless otherwise specified.

EXAMPLES

Example 1

1H-Pyrazole-1-carboxamidine Hydrochloride

In a 500 ml four-necked flask fitted with gas inlet tube and gas outlet tube, internal thermometer and reflux condenser with in each case two safety wash bottles connected upstream and downstream, 34.1 g (0.5 mol.) of pyrazole and 21.0 g (0.5 mol.) of cyanamide are dissolved in 330 ml of dimethoxyethane. At 80° C., dry hydrogen chloride gas is introduced into the reaction solution at a rate of about 15 l/h for about 50 minutes. The solution is then allowed to cool and the precipitated solid is removed by filtration. The product obtained is dried under reduced pressure (100 mbar, 80° C.) to give 1H-pyrazole-1-carboxamidine hydrochloride in the form of a colorless, finely crystalline solid. Yield: 70.6 g (96%), melting point: 160 to 168° C. (literature: 165 to 166° C.) $^{13}$C-NMR (DMSO-$d_6$) δ 152.3, 146.0, 131.5, 111.9.

Example 2

3,5-Dimethyl-1H-pyrazole-1-carboxamidine Hydrochloride

Preparation and work-up of the reaction are conducted is a manner similar to Example 1. 48.1 g (0.5 mol.) of 3,5-dimethypyrazole and 21.0 g (0.5 mol.) of cyanamide are dissolved in 330 ml of dimethoxyethane. At 80° C., gaseous hydrogen chloride is introduced therein for 50 minutes. The result is the product 3,5-dimethyl-1H-pyrazole-1-carboxamidine hydrochloride which is obtained as a colorless crystalline solid.

Yield: 82 g (94%)

The melting point is 148-150° C. (literature: 150° C.)

The disclosure of German priority application having Serial No. 100 50 900.2 filed Oct. 13, 2000 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process for preparing 1-guanylpyrazole acid adducts of the formula:

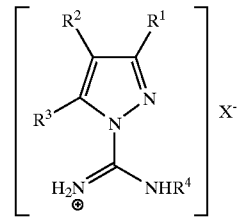

wherein $R^1$, $R^2$ and $R^3$ independently of one another are hydrogen, a branched or straight-chain $C_{1-6}$-alkyl group, a $C_{3-8}$-cycloalkyl group or a $C_{6-12}$-aryl group which is unsubstituted of substituted by 1 to 6 alkyl groups;

$R^4$ is hydrogen or a straight-chain or branched $C_{1-4}$-alkyl group; and

X is Cl or Br, which comprises:
conducting the reaction of pyrazole or a derivative thereof with cyanamide or a derivative thereof and gaseous hydrogen chloride or hydrogen bromide in an aprotic solvent, with the proviso that p-dioxane is excluded as an aprotic solvent.

2. The process as claimed in claim 1, wherein the reaction is conducted in a solvent selected from the group consisting of sulfoxides, sulfones, sulfolanes, chlorinated hydrocarbons, ketones, ethers, nitrites and polyethers.

3. The process as claimed in claim 2, wherein the chlorinated hydrocarbon is 1,2-dichloroethane, dichloromethane or trichloromethane.

4. The process as claimed in claim 2, wherein the reaction is conducted in dimethyl sulfoxide, diisopropyl sulfone, sulfolane, 2-methylsulfolane, 3-methyl sulfolane or 2-methyl-4-butylsulfolane.

5. The process as claimed in claim 2, wherein the reaction is conducted in acetone, methyl ethyl ketone, methyl isobutyl ketone or cyclohexanone.

6. The process as claimed in claim 2, wherein the reaction is conducted in methyl tert-butyl ether, diphenyl ether, diisopropyl ether, anisole, dimethoxyethane or diethylene glycol dimethyl ether.

7. The process as claimed in claim 2, wherein the reaction is conducted in acetonitrile.

8. The process as claimed in claim 1, wherein the reaction components are reacted at a pressure ranging from 0.1 to 50 bar, a reaction temperature ranging from −20° C. to 150° C. and reaction times ranging from 15 minutes to 8 hours.

9. The process as claimed in claim 8, wherein the reaction components are reacted at a pressure of about 1 to 10 bar, a reaction temperature ranging from 0° C. to 100° C. and a reaction time ranging from 30 minutes to 4 hours.

10. The process as claimed in claim 9, wherein the reaction components are reacted at a pressure of about 1 bar, a reaction temperature ranging from 60° C. to 90° C. and a reaction time ranging from 45 minutes to 60 minutes.

11. The process as claimed in claim 1, wherein the carboxamidine hydrochloride or carboxamidine hydrobromide obtained is separated in a mechanical separating operation and, thereafter, optionally, subjected to thermal after-treatment.

12. The process as claimed in claim 1, wherein the reaction is conducted batchwise or continuously.

* * * * *